United States Patent [19]
Ykema et al.

[11] Patent Number: 6,165,757
[45] Date of Patent: Dec. 26, 2000

[54] NITROGEN FEED IN STATIN FERMENTATION

[75] Inventors: Adriaantje Ykema, Leiden; Jennifer May Lindsay, Voorburg, both of Netherlands

[73] Assignee: DSM N.V., Netherlands

[21] Appl. No.: 09/367,710

[22] PCT Filed: Feb. 20, 1998

[86] PCT No.: PCT/EP98/01123

§ 371 Date: Sep. 15, 1999

§ 102(e) Date: Sep. 15, 1999

[87] PCT Pub. No.: WO98/37220

PCT Pub. Date: Aug. 27, 1998

[30] Foreign Application Priority Data

Feb. 20, 1997 [EP] European Pat. Off. ............... 97301119

[51] Int. Cl.[7] .............................. C12P 17/06; C12P 7/62; C12P 39/00
[52] U.S. Cl. ............................ 435/125; 435/42; 435/135; 435/136
[58] Field of Search ............................ 549/292; 435/125, 435/42, 53, 135, 136

[56] References Cited

FOREIGN PATENT DOCUMENTS

WO 9706128  2/1997  WIPO.

OTHER PUBLICATIONS

XP002036624, Hosobuchi, et al, Biosci. Biochem. pp. 1414–1419 1983.
XP00203665, Hosobuchi, et al, Biotechnology., vol. 42, pp. 815–820.
XP002036626,Gbewanyo et al, Biotech.. vol. 37, pp. 1101–1107 1991.
XP002036627. Chem.Abstracts. vol, 123, Jul. 1995., No. 3 (1 page) p. 700.
XP002036628, Chem.Abstracts., vol, 115, Dec. 1991, p. 037, No. 25.

*Primary Examiner*—Amelia Owens
*Attorney, Agent, or Firm*—Bierman, Muserlian and Lucas

[57] ABSTRACT

A fermentation process is disclosed for producing an HMG-CoA reductase inhibitor such as lovastatin or compactin. In particular, it relates to a process wherein at least part of the assimilable nitrogen source and, optionally, the carbon source is provided continuously or intermittently to the culture.

18 Claims, No Drawings

NITROGEN FEED IN STATIN FERMENTATION

This application is a 371 of PCT Application EP98/01123 filed Feb. 20, 1998.

FIELD OF THE INVENTION

The present invention relates to a fermentation process for the production by microorganisms of compounds which are HMG-CoA reductase inhibitors, such as lovastatin and compactin. In particular, it relates to a process where an assimilable source of nitrogen or nitrogen and carbon is provided continuously or intermittently.

BACKGROUND OF THE INVENTION

A wide variety of relatively complex molecules, in particular drugs, can be produced by microorganisms during a fermentation process. Usually, the microorganism is fed with various assimilable sources of the elements required for the organism to produce the desired product.

The efficiency of production depends on a large number of factors, not least the nature of the carbon sources and the further conditions of fermentation. U.S. Pat. No. 4,231,938 (Merck) describes the cultivation of an Aspergillus microorganism in order to produce lovastatin.

U.S. Pat. No. 4,323,648 (Sankyo) also describes a process for the production of lovastatin this time using a microorganism of the genus Monascus.

Finally, U.S. Pat. No. 4,049,495 (also Sankyo) refers to the production of compactin using a Penicillium microorganism.

Buckland et al, Novel Microbial Products for Medicine and Agriculture, Eds. Demain et al, Chapter 19, 161–169 (1989, Society for Industrial Microbiology) describes the production of lovastatin by *Aspergillus terreus*. Fermentation development studies showed that for high lovastatin production, pH control and slow use of the carbon source was essential.

Although all of these documents refer to the production of various drugs by culturing different microorganisms, there are a number of problems associated with these processes. Most of them describe batch fermentation processes where the nutrients are added or mixed in with the microorganism in the culture medium at the beginning of the production process. Generally, (the fixed amount of) these nutrients are therefore gradually used up during fermentation. However, at the beginning of the process, because the nutrients are at relatively high concentrations, production of the drug is low because the microorganisms use carbon and nitrogen sources to grow, rather than to produce the drug. In such a process the rate of production of the drug is largely uncontrollable.

Overall production levels are low because in the batch processes nutrients are in effect supplied only once to the microorganism and so no variation (at least during production) can be conducted to balance growth of the biomass with production of the fermentation product.

The main objective of the invention is to provide a fermentation process that provides a greater degree of control and/or flexibility over production, so that the manufacturer can vary conditions to optimise production of the desired fermentation product. Surprisingly, it was found that feeding a nutrient not used to build up the compound of interest does increase the yield of the fermentation.

DESCRIPTION OF THE INVENTION

Therefore, according to a first aspect of the present invention, there is provided a (fermentation) process for the production of a compound of the general formula:

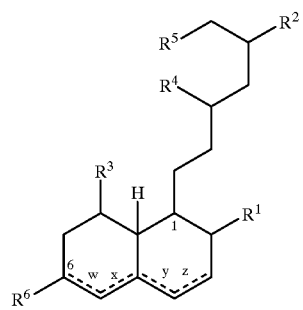

wherein:

each of $R^1$ and $R^2$ independently represent a hydrogen atom, a hydroxy, $C_{1-10}$ alkyl, $C_{1-10}$ alkoxy, $C_{3-10}$ cycloalkyl or $C_{6-10}$ aryl group or a $C_{7-11}$ aralkyl group optionally containing one or more hetero atoms;

$R^3$ represents $R^1CO$— or $R^1C(O)O$—;

each of $R^4$ and $R^5$ independently represent a hydrogen atom, —$COOR^1$ (except that then $R^1$ is not a hydroxy or alkoxy group), —$OR^1$ or —$COR^1$ or, when combined, complete a six-membered ring having one or two oxygen heteroatoms;

$R^6$ represents a hydrogen atom, or a $C_{1-10}$ alkyl or hydroxy group;

wherein each of the alkyl, alkoxy, cycloalkyl, aryl and/or aralkyl groups can be optionally substituted with one or more halogen atoms, trifluoromethyl, hydroxy or $C_{1-4}$ alkoxy groups;

and w, x, y and z each represent none, 1, or 2 double bonds;

or a salt and/or isomer thereof;

the process comprising culturing a microorganism in a culture medium comprising an assimilable nitrogen (N) source and an assimilable carbon (C) source under fermentation conditions that allow the microorganism to produce the compound, wherein at least part of the nitrogen source is supplied to the culture continuously or intermittently. The carbon source may also be supplied to the culture continuously or intermittently.

The invention at its broadest therefore contemplates a fermentation process for the production of a compound of formula (I) wherein at least one addition of the nitrogen source occurs after the fermentation process has begun.

By a source, as for instance nitrogen source or carbon source, is meant one or more compounds able to deliver nitrogen or carbon useful for the fermentation process, as for instance ammonia and yeast extract or glucose and glycerol, respectively.

A second aspect of the invention relates to a (fermentation) process for the production of a compound of formula I, the process comprising culturing a microorganism in a culture comprising an assimilable nitrogen source and an assimilable carbon source under fermentation conditions that allow the microorganism to produce the compound, wherein the nitrogen and optionally the carbon sources are supplied to the culture medium at substantially the same rate as they are consumed by the microorganisms present in the culture.

The continuous or intermittent supply (of the nitrogen and, optionally also, carbon source to the culture, which comprises the microorganisms) preferably takes place during at least part of the fermentation process, although preferably this will occur for at least 30%, but usually at least 50%, and optimally for at least 75% of the production process.

Besides that, it was surprisingly found that the processes of the invention can lead to higher yields than in the prior art, especially as the compounds produced do not contain nitrogen and so would be expected to be relatively unaffected by the amount or mode of supply of the nitrogen source.

In the invention the nitrogen and carbon source(s) can be supplied to the culture at different rates: these rates can be increasing, decreasing or constant or combinations thereof during the fermentation. These rates can be changed during the fermentation independently of each other. In the second aspect the rate can be substantially the same as that which the or each source is consumed by the microorganisms. This may be achieved by making the rate of supply of the (or each) source alterable according to the number or weight of the microorganisms (being supplied).

The composition that is supplied to the culture over time is often called a "feed". In some processes, both the C and N sources may be present in a single feed vessel.

Preferably, however, there are at least two feeds, and suitably the C and N sources are supplied independently from separate feed vessels. There may be two reasons for this. A first advantage is that it allows the operator to vary the relative amounts of C and N supplied during the process. The second is that the C and N sources may be subject to different sterilisation conditions, and therefore it is easier to sterilise each source separately, under conditions appropriate for that source.

Thus the nitrogen and the carbon sources can be supplied (or added) separately or supplied simultaneously and/or as a combined preparation. The or each composition or feed can be a solid or, more usually, a liquid.

If the supply is intermittent, it is preferred that the feed source is supplied in aliquots. That is to say, the same amount of the relevant source is supplied whenever supply occurs.

Preferred C/N (weight) ratios supplied to the culture are at least 5:1, preferably at least 10:1, optimally from 10:1 to 130:1. More suitable C/N ratios are from 15:1 to 60:1, such as from 20:1 to 50:1. However, this C/N ratio may be varied to change production conditions during production of the compound. This can be achieved by varying the ratio of the rate of supply of the nitrogen and carbon feed sources or even stopping the supply at certain times or by varying the ratio of concentrations of these feed sources relative to each other.

The C/N ratios quoted in this specification are usually calculated on the basis of weight. However, as will be appreciated, the molar ratio will be similar because of the similar molecular weights of these two elements (12 and 14, respectively). These amounts are calculated on the basis of the amount of carbon in the carbon source, and nitrogen in the nitrogen source fed to the culture, that is consumable by the microorganism. This is important for complex sources of carbon and/or nitrogen, which may contain carbon and/or nitrogen containing compounds that are not assimilable by the microorganism.

The nitrogen and/or carbon sources can be suitably added to the culture medium immediately as fermentation begins, or shortly thereafter. In the invention at least one addition of the nitrogen source takes place after fermentation has begun. The supply can be continuous (in which case there is no interruption in the supply) or it can be intermittent (where time gaps or breaks in the supply can occur, for example one may have a continual supply). If supply of one or both sources is intermittent, then there should be at least two, such as five, and preferably at least ten, additions to the culture of the nitrogen or nitrogen and carbon source (via the feed).

It is preferred that the concentration of the assimilable nitrogen source in the culture is kept to a minimum during the production phase. Indeed, one aim is to supply the nitrogen source (and possibly also the carbon source) at a rate that is approximately the same (or in some cases even lower than) the rate of consumption of the nitrogen or nitrogen and carbon sources by the microorganisms in the culture (this mixture of microorganisms and medium is often referred to in the art as the "broth" and is not to be confused with the (usually sterilised) feed composition(s) added to the culture during production). If this is achieved then it will be apparent that, apart from the initial amounts of the carbon and nitrogen sources, one will aim to have a concentration, over time, as close as possible to zero of the nitrogen or nitrogen and carbon sources.

A wide variety of different nitrogen and carbon sources is available, and can be used in the process of the invention. However, the most appropriate source depends not only upon the microorganism employed, but also the compound which is to be produced as a result of the fermentation. The preferred carbon and/or nitrogen sources are usually (but not always) added in a state of a high degree of purity, and are common chemicals that can therefore be obtained from well known chemical suppliers (for example one is Sigma in Poole, Dorset, United Kingdom).

Optionally a single chemical will act as the source for the nitrogen and/or carbon source. In other words, each of the carbon and/or nitrogen source is only one compound. As will be realised, this is in contrast to complex nitrogen and/or carbon sources which, although they can be used, are usually natural extracts and contain, in addition to these sources, a wide variety of other substances. Since it can be difficult to determine their precise carbon and/or nitrogen content it is preferred that a purified chemical is used as the appropriate source (which may allow better controllability over the process). Hence optimising production conditions can be much easier, because the precise amount of nitrogen and carbon being delivered can be easily calculated, and furthermore natural extracts may contain additional substances that can adversely affect production or may contain non-consumable sources of nitrogen and/or carbon (ie. ones that cannot be used by the microorganism). In addition, the chemical (e.g. synthetic) sources can be more easily transported, for example pumped, which is unlike many natural sources which are relatively thick and viscous. Natural sources can also vary in content from batch to batch, and furthermore may vary in content depending on the season.

Preferred nitrogen and/or carbon sources are water soluble or water miscible, and are usually sterilised before supply to the culture medium.

Suitable complex nitrogen sources can comprise, for example, yeast hydrolysates (or autolysed yeast or yeast RNA), primary yeast, soybean meal, cotton seed flour, hydrolysates of casein, corn steep liquor, distiller's solubles, tomato paste, peptone, meat extract, yeast, yeast extract, beef extract, peanut meal, rice bran and/or fish meal.

Alternatively, inorganic nitrogen sources, such as nitrate or ammonia, or organic nitrogen sources, such as urea or an amino acid (e.g. asparagine), can be used.

The preferred nitrogen source is however ammonia (or ammonium ions). The ammonia can be supplied in the form of an ammonium salt or as a source of ammonium ions, for example ammonium nitrate, ammonium sulphate or ammonium phosphate or, more preferably, as ammonia (for example, as ammonium ions solution, such as an aqueous or alcoholic solution).

The use of ammonia may provide several advantages. Firstly, ammonia is easily dissolvable, unlike soya bean or corn steep liquor, which both form relatively thick and viscous liquids. A further advantage of ammonia is that it can act as a pH regulant. If ammonia is not used as the nitrogen source, then a pH regulant may need to be added, and this can be any suitable base other than ammonia, for example an alkali metal hydroxide such as e.g. sodium hydroxide.

As for the carbon source, this can comprise dextrose, maltodextrin, dextrin, oat flour, oat meal, molasses, citrate, acetate, soybean oil, vegetable oil, glycerol, malt extract, cod liver oil, starch, molasses, ethanol, (sodium) ascorbate, lard oil, soya bean oil or cotton seed oil. However, a preferred carbon source is a carbohydrate and/or sugar, for example fructose, maltose, sucrose, xylose, mannitol, glucose, lactose, glycerine and/or starches and grains such as oat, rye, cornstarch, or corn meal.

The amount of nitrogen or nitrogen and carbon source to be supplied to the culture will be influenced by a number of factors, including not only the type of microorganism used, but also the level of production desired and various other fermentation conditions (e.g. oxygen transfer capacity of the fermenter).

The rate of supply of the nitrogen source is preferably at least 1 mmol N per kg broth per hour. In terms of weight of nitrogen, the rate of supply of N is suitably from 2 to 200 such as 5 to 50, optimally from 5 to 30 mg/kg broth/hour, but can be much higher and can be as much as conditions allow, for example bearing in mind the preferred C:N ratios.

In view of the Applicant's prior International Application number PCT/EP96/03495 (WO-A-97/06128), the process of the invention may not include the continuous supply of 3.5 mg nitrogen per kg of culture per hour.

When the nitrogen source is ammonia, this is preferably present in the culture at no more than 500 mg/l, preferably no more than 50 mg/l.

Apart from varying the rate of supply of the nitrogen source one can add to the feed solution or culture medium a substance which can directly or indirectly affect the concentration of that nitrogen source. One example of this is to add a substance that can absorb ammonia, so reducing its concentration, for example a zeolite. Other ammonia absorbing substances include those capable of precipitating ammonia as a complex salt, for example as ammonium magnesium phosphate.

If the carbon source is glucose, then this is preferably supplied at a rate of at least 3, suitably at least 6, optimally from 5 to 8 mmol glucose per kg broth per hour. In terms of weight of glucose, this is preferably from 0.5 to 2.0, suitably from 0.7 to 1.7, optimally from 1.1 to 1.5 g/kg broth/hour. Usually the amount of glucose supplied will be as high as possible, with consideration of the oxygen transfer and mixing capacity of the fermenter vessel containing the broth.

When the carbon source is glucose, the concentration in the culture medium of glucose is suitably from 0 to 40, preferably 0 to 10, optimally 0 to 2 g/l. In terms of molar concentrations, the glucose is preferably present in the culture medium (or broth) at from 0.5 to 3.0, preferably from 1.0 to 2.3, optimally from 1.5 to 2.0 mmol/l.

The biomass concentration can be varied according to the desired production conditions. However, usually it will be from 10 to 150, preferably from 20 to 100, and optimally from 30 to 70, g/l (of culture medium or broth).

Discussion has so far concentrated on the supply of additional substances to the culture medium during production process. However, in addition part of the culture medium (which may include some microorganisms, or part of the biomass) may be removed during the production phase. This may be at regular time intervals (for example intermittently) or there may be a constant removal, in which case this occurs continuously. The culture medium can thereby be replenished with fresh ingredients, preferably corresponding to the amount of one or more particular ingredients that have been withdrawn.

Apart from the assimilable carbon and nitrogen sources, the culture medium used during fermentation can be provided with a variety of other ingredients, suitably to increase production. Thus the culture medium may additionally comprise one or more inorganic salts and/or trace elements, and potentially also an antifoaming agent. Inorganic salts include phosphates sulphates and/or chlorides, for example potassium hydrogen phosphate, sodium sulphate, magnesium sulphate and/or calcium chloride.

Phosphates may be added as a mixture of primary and or secondary salts of potassium and/or sodium, the ratio and quantity depending on pH and buffering capacity required.

The trace elements are often metals, such as transition metals. These may include zinc, magnesium, cobalt, calcium and/or iron. For example, these may be added in the forms of zinc chloride, manganese sulphate and/or iron (III) sulphate. The trace metals, in particular, calcium, molybdenum and/or cobalt, may be added as chloride salts, but preferably as sulphate salts.

The culture medium may additionally be supplied with what are termed in the art as structural and/or catalytic elements.

Structural elements are those elements which are in general constituents of microbial macromolecules, for example hydrogen, oxygen, carbon, nitrogen, phosphorous and sulphur. Of these, hydrogen, oxygen, carbon and nitrogen are, preferably, contained within the carbon and/or nitrogen source. Phosphorous and sulphur are often added separately, as phosphate, sulphate and/or thiosulphate ions.

Catalytic elements are, generally speaking, elements that are constituents of enzymes or enzyme cofactors. These include magnesium, iron, copper, calcium, manganese, zinc, cobalt and/or selenium.

In addition to the structural and/or catalytic elements, cations, such as potassium and/or sodium, are preferably present. These can function as counter ions and may assist in the control of intracellular pH and osmolarity. Additional substances that may be present in the culture medium include chelating agents, such as citric acid, and/or buffering agents, for example mono-and di-potassium phosphate, and calcium carbonate. Buffering agents are usually added when the process does not have an external pH control.

Alternatively or in addition, an anti-foaming agent may be added to the culture medium. Preferably no anti-foaming agent is present in any of the feed compositions, but if it is provided it is less than 10 ml, preferably less than 5 ml, optimally less than 1.0 ml, per kg. The antifoaming agent may be added in some processes at from 0.05 to 0.5 ml per kg. Suitable agents include polypropylene glycol, soybean oil or silicone or a mixture thereof.

Vitamins are often necessary for the normal metabolism of microorganisms, and so should be added to culture medium containing a microorganism that is not capable of synthesizing the vitamins (or to an insufficient extent)

required for production. Vitamins contemplated include thiamin, riboflavin, pyridoxal, nicotinic acid or nicotinamide, pantothenic acid, cyanocobalamin, folic acid, biotin, lipoic acid, purines, pyrimidines, inositol, choline, and/or hemins.

A preferred culture medium will therefore comprise a carbon source, a nitrogen source, phosphate, sulphate, desired cations, catalytic elements and, optionally, one or more chelating agents, buffering agents and vitamins.

The fermentation process is relatively simple, and can be conducted by a person skilled in the art. There are, however, a number of conditions which, if followed, can provide increased production.

The first is pH. This should preferably be kept constant throughout the fermentation process. This can be achieved by using a buffered culture medium, or by using a balance of acid and alkali. Suitable chemicals are sulphuric acid and sodium hydroxide. The pH is usually from 3.5 to 10.0, with the optimum dependent on the microorganism used and/or compound to be produced. However, as a guide, the pH is (e.g. for lovastatin) preferably from 5.0 to 8.0, optimally from 6.0 to 7.0. Alternatively, the pH can be controlled by other means, for example by using ammonia, which can then act not only as the nitrogen source but also as the pH controlling agent.

The temperature can affect production and so is usually from 20 to 32° C., preferably (e.g. for lovastatin) from 25 to 30° C., and optimally from 27 to 29° C.

Better production can be achieved by providing air (aeration) to the culture medium during the fermentation process. This can be added to the vessel directly above the culture medium or bubbled through at least part of the culture medium. Aeration can be important in certain circumstances as production can be slow if the microorganisms are not provided with sufficient oxygen. Usually the volume of air supplied is from 0.3 to 1.5 volume units per unit volume of broth per minute (vvm), preferably from 0.6 to 1.2, such as from 0.8 to 1.0. Optimal supply is from 0.5 to 0.7 vvm. The overpressure (in the main fermenter) is preferably from 15 to 20 psi.

Alternatively or in addition to aeration, the broth can be agitated. This can be achieved in various ways, although agitation by stirring is often preferred.

Suitable impellers are of hydrofoil axial flow design, which may create upward hydrodynamic thrust during rotation, which can increase the downward pumping capacity of the blades. These are available from Prochem Mixing Equipment Ltd, Brampton, Ontario, Canada. Alternatively, an agitator where the liquid culture medium is forced radially outwards from the impeller can be used (a Rushton turbine, in which case it can be at an intensity of from 0.5 to 2.0 Kw/tonne). The speed of these agitators is not particularly critical, but can for example be from 200 to 1000, preferably from 300 to 700, optimally at about 500 rpm for laboratory scale processes. For industrial size fermentations the stirrer speed can be from 20 to 80, such as from 40 to 60, optimally about 50, rpm.

One of the principal reasons why aeration and agitation is important is to keep the oxygen content of the culture medium high. This should preferably be at least 10%, such as at least 20% (in terms of $O_2$ saturation). Preferably agitation and/or aeration should keep the oxygen concentration above 0.2 mmol/l. Good mixing of the culture medium improves production, and is suitably achieved using both aeration and agitation.

The microorganisms can be subjected to various processes before (the main) fermentation takes place, and this can include one or more growth phase(s). It is common practice in the art to grow the microorganisms, to obtain a sufficiently large amount of biomass ready for the production process. There may be only one growth phase but, in preferred processes, there are two or three growth phases before fermentation. During these growth phases the microorganism can be provided with one, or more, or even all, of the various additives mentioned for the culture medium. These growth phases are sometimes referred to in the art as "seed phases".

Fermentation is suitably initiated in a sterilised vessel. After the microorganism has been subjected to one or more growth phases, it is then added to the fermentation vessel. If there is more than one seed (or growth) phase(s), then usually all (although it can be a fraction) of the microorganisms from the previous seed (or growth) stage are used to inoculate the next medium.

Any suitable fermentation vessel can be used, although a conventional aerobic fermentation vessel will suffice, preferably provided with means for agitation and/or aeration.

Although the compound can be produced by microorganisms both at the surface (e.g. in a solid state) and submerged (or submersed) in the culture medium it is preferable to conduct the production in the submerged state. Fermentation can thus be conveniently carried out by inoculating a suitable nutrient medium with the microorganism and allowing production to proceed. This production phase may take from 12 to 600, preferably from 18 to 400, optimally from 24 to 200 hours.

Suitable compounds of formula I can be pharmaceuticals or drugs and/or can have physiological effects, such as those belonging to the class of compounds known as statins. These include lovastatin, simvastatin, pravastatin and compactin. Simvastatin can be obtained, by chemical synthesis, from lovastatin. Pravastatin can be produced from compactin by a fermentation process, using a different microorganism from the one able to produce compactin, or the same microorganism if able to do so. The formulae of these compounds are shown below.

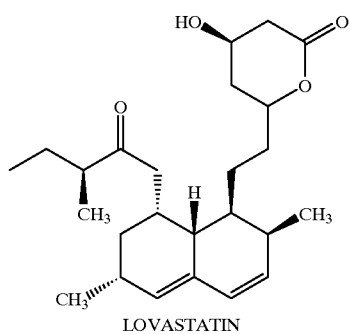

LOVASTATIN

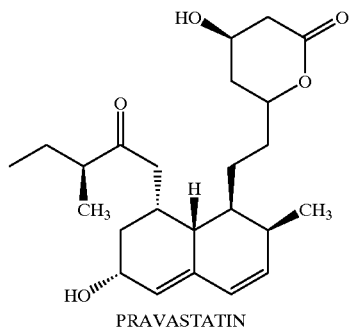

PRAVASTATIN

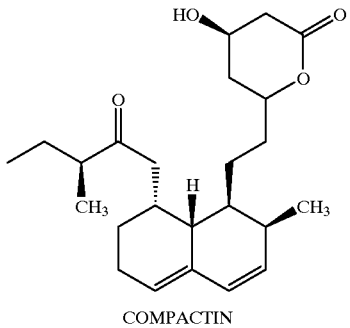

COMPACTIN

Simvastatin which has the same structure as lovastatin except that the 1-methyl propyl group (after the carbonyl moiety) is replaced by a 1,1-dimethyl propyl group.

Even more preferred are those compounds that are hydroxymethylglutaryl-coenzyme A (HMG-CoA) reductase inhibitors. Such compounds can reduce cholesterol levels and/or find use as anti-hypocholesterolemic agents, especially for treating atherosclerosis and ischemic heart disease.

In the compounds of formula I the alkyl and alkoxy groups (either alone or as part of a larger group) can be either straight or branched. Alkyl groups are preferably $C_{1-4}$ alkyl groups, for example methyl or ethyl. Alkoxy groups are preferably methoxy or ethoxy groups.

Preferred cycloalkyl groups are pentyl or hexyl groups. Suitable aryl groups include phenyl or naphthyl.

Preferably $R^1$ represents a hydrogen atom or, optimally, a methyl group. Preferably $R^2$ represents a hydroxy group. $R^3$ preferably represents —OC(O)$R^1$, where $R^1$ is a $C_{1-10}$ alkyl group, for example a $C_{1-4}$ alkyl group. In preferred compounds (the statins) $R^3$ represents a 2-methyl butyrate group (—$CH_2C(O)CH(CH_3)C_2H_5$).

$R^4$ preferably represents a hydroxy group and/or $R^5$ preferably represents —COO(H). When $R^4$ and $R^5$ are not combined the compound of formula (I) is in the acid form: this can be converted to the lactone form by ring closure, so that $R^4$ and $R^5$ when combined together can form a 6-membered ring containing one or two oxygen heteroatoms. Here $R^4$ and $R^5$ combined preferably represent —C(O)O—.

$R^6$ preferably represents a hydrogen atom or a methyl or hydroxy group. It is preferred that two double bonds are present: in this situation, generally double bonds will be in the locations w and y or x and z.

Compounds where $R^6$ represents a hydrogen atom can be converted to those where $R^6$ represents a hydroxy (HO) group by a hydroxylation reaction e.g. performed by the hydroxylase enzyme. In this way compactin can be converted to pravastatin.

The various isomers of compounds of formula (I) are included within the formula and this of course includes stereoisomers. The compounds preferably have the stereoisomerism of pravastatin or compactin, as appropriate. Salts include acidic and/or basic salts formed with inorganic and/or organic bases. Non-toxic, pharmaceutically acceptable salts are preferred.

After fermentation, the compound can be isolated from the culture medium. This can be achieved using standard techniques, but will usually comprise a filtration to separate the biomass, to produce a filtrate, followed by chromatography. Chromatographic techniques include adsorption to a hydrophobic resin, ion exchange, column chromatography. Solvent extraction may be performed using an alcohol (e.g. methanol) and/or ethyl acetate.

In a preferred process, to assist isolation of e.g. lovastatin the pH of the culture medium during or after production can be increased (i.e. made particularly alkaline) if preferred. It has been found that if the pH is above about pH 10, for example between pH 10 and pH 13, and optimally between pH 11 and pH 12.5, the 4-acetyl lovastatin produced by the microorganism can be converted into lovastatin itself, instead of being converted into dehydrolovastatin via the dehydration that occurs for pure 4-acetyl lovastatin. In addition, under these conditions the 2-methyl butanoate group may not be removed during the production process. Preferably the temperature of this stage is at least 50° C., such as between 60 and 95° C. This is conducted on the clarified broth filtrate which results after removal of the biomass from the culture medium during fermentation.

The compound may be subjected to further chemical treatment during, although more usually after, the production phase(s). The compound is usually, although not exclusively, isolated before further treatment. This is because in the case of some microorganisms the compound produced is not the final chemical that is desired. For example, organisms of the genus Aspergillus produce lovastatin in the free hydroxy acid form. This is then converted to lovastatin, which is the final drug, which can then be used in the preparation of a medicament. Thus in the case of lovastatin, the microorganism usually produces the compound in the hydroxycarboxylate (open lactone) form. This compound can be isolated, along with any salt forms. The hydroxy acid form can then be converted to the lactone form (lovastatin).

The processes of the invention are applicable to a wide range of microorganisms. These include fungal microorganisms, such as of the genus Aspergillus, although others include Penicillium, Hypomyces, Paecilomyces, Eupenicillium, Trichoderma, Monascus, Phoma, Doratomyces, Gymnoascus or Pleurotus, and bacteria, e.g. filamentous bacteria, for example of the genus Actinomycetes. These organisms can produce lovastatin, simvastatin, pravastatin (eptastatin) or compactin.

Preferred organisms contemplated by the invention, and the fermentation products that they produce, are listed as follows.

Genus/Products

Aspergillus Antihypercholesteremic agents;

Products for treating atherosclerosis and hyperlipidaemia

Monascus

Antihyperlipaemic and anticholesteremic agents

Penicillium

Inhibitors of cholesterol biosynthesis;

antiatherosclerosis and antihyperlipaemia agents

Taking the Aspergillus genus first, preferred strains are *Aspergillus terreus* such as those microorganisms designated MF-4833 deposited under Accession No. ATCC No.20541 and microorganism MF-4845, deposited under Accession No. ATCC No.20542. These microorganisms can produce lovastatin and are described in U.S. Pat. No. 4,231,938.

Microorganisms of the genus Monascus can also produce lovastatin. Included are *M. anka, M. purpureus, M. ruber, M. vitreus* and *M. paxii*. Preferred strains include SANK 15177, SANK 10671, SANK 13778 and SANK 18174. All these strains are described in U.S. Pat. No. 4,323,648.

Turning now to the genus Penicillium, the compounds that can be prepared by these microorganisms using the process of the present invention are described in U.S. Pat. No. 4,049,495. These are preferably of the strain *P. citrinum*, such as strain ATCC 38065. These microorganisms can be used to prepare compactin and lovastatin.

Particularly preferred are microorganisms of the class *Aspergillus terreus,* for example strain AD 43, DS No. 28373, which has been deposited with the Culture Collection at Centraal Bureau, voor Schimmelcultures (CBS, Delft, The Netherlands), under Accession No. CBS 456.95. This microorganism is capable of producing lovastatin and is mentioned in the following Examples.

The microorganism can be a wild type or naturally occurring strain. However, the microorganism may be genetically engineered and/or altered from the wild (or natural) type. These microorganisms may be produced by a classical mutagenesis treatment using UV radiation or a suitable chemical mutagen or may have one or more genes removed, and/or one or more (heterologous) genes inserted.

The invention in a further aspect relates to a pharmaceutical composition produced by the process of the invention and a pharmaceutically acceptable carrier or excipient.

The invention will now be described, by way of example, with regard to the following Examples which are provided for means of illustration and are not to be construed as limiting.

EXAMPLE 1

*Aspergillus terreus* strain AD43, DS-number 28373 has been deposited with the Centraal Bureau voor Schimmelcultures (CBS, Delft, The Netherlands), and has been granted CBS Accession No. CBS 456.95.

One 1 ml vial of a spore suspension of *Aspergillus terreus* strain AD43, stored in glycerol at −80° C. was opened aseptically, and the contents suspended in a 2 liter shake flask containing 500 ml of the following medium (500 ml, sterilised for 20 minutes at 120° C.):

| Ingredient | Amount per kg |
| --- | --- |
| Glucose | 75 g |
| Yeast extract | 12 g |
| Glycerol | 5 ml |
| KH$_2$PO$_4$ | 4 g |
| Sodium acetate | 1 g |
| FeSO$_4$.7H$_2$O | 5 mg |
| Soybean oil | 2 ml |

The shake flask was incubated at 28° C. during 48 hours in a rotary shaker at 280 rpm (first growth phase), after which 20 ml was inoculated into a fermenter with 10 kg of medium. The composition of the fermentation broth, before inoculation, was as follows (after sterilisation for 60 minutes at 120° C.):

| Ingredient | Amount per kg |
| --- | --- |
| Glucose | 20 g |
| Yeast Extract | 11.8 g |
| KH$_2$PO$_4$ | 1.75 g |
| Na$_2$SO$_4$ | 0.5 g |
| MgSO$_4$.7H$_2$O | 0.7 g |
| CaCl$_2$.2H$_2$O | 0.06 ml |
| Antifoam agent (polypropylene glycol) | 0.1 ml | and small amounts of the trace elements ZnCl$_2$ (1 mg) MnSO$_4$.1H$_2$O (0.5 mg), FeSO$_4$.7H$_2$O (1.4 mg) and citric acid (0.6 g).

Fermentation was begun with the conditions as follows:

pH was kept constant at 6.5, using H$_2$SO$_4$ and NaOH;

temperature was 28° C.;

air supply was 0.9 volume air per volume broth per minute;

the broth was agitated.

This was continued for about 40 hours.

When all the glucose was consumed a glucose and ammonia feed were started at the following rates:

glucose 1.35 g glucose per kg (of initial) broth per hour;

ammonia 28.6 mg nitrogen in the form of NH$_3$ per kg (of initial) broth per hour.

The glucose and the ammonia were fed in separate aqueous solutions convenient for accurate dosing. After 7 days of feeding the fermentation finished. The production of lovastatin is shown in Table 1. The yield of lovastatin was 16% higher than that of Comparative Example 6.

TABLE 1

| Example | C/N fed (g C/g N) | Lovastatin acid mg/l | % relative to Example 6 |
| --- | --- | --- | --- |
| 1 | 19 | 290 | 116 |
| 2 | 38 | 400 | 160 |
| 3 | 45 | 290 | 116 |
| 4 | 34 | 355 | 142 |
| comp 5 | — | 260 | 104 |
| comp 6 | — | 250 | 100 |

EXAMPLE 2

The complete procedure of Example 1 was followed, except with one difference: the ammonia was fed at a rate of 14.3 mg nitrogen per kg broth per hour. The lovastatin acid concentration at the end of fermentation was 140% of the lovastatin acid concentration produced in Example 1 (see Table 1). The yield of lovastatin was 60% greater than that from Comparative Example 6.

EXAMPLE 3

The initial procedure of Example 1 was followed and after the first growth phase 20 ml of the seed culture was inoculated into a fermenter with 10 kg of medium. The composition of the fermentation broth was as follows (it was first sterilised for 20 minutes at 120° C.):

| Ingredient | Amount per kg |
| --- | --- |
| Glucose | 23.2 g |
| Yeast Extract | 13.3 g |
| Antifoam agent (polypropylene glycol) | 0.1 ml |

Fermentation was begun with conditions as follows:

pH was kept constant at 6.5, using H$_2$SO$_4$ and NaOH;

temperature was 28° C.;

the broth was agitated and aerated.

This was continued for about 40 hours.

When all the glucose was consumed a glucose and yeast extract feed was started at the following rates:

glucose 1.2 g glucose per kg (of initial) broth per hour;

yeast extract 10.7 mg nitrogen in the form of yeast extract per kg (of initial) broth per hour (the extract contained 8.5% by weight of nitrogen).

The glucose and the yeast extract were both fed as one single aqueous solution which allowed for accurate feeding.

After 7 days of feeding the fermentation finished; the production of lovastatin is shown in Table 1.

EXAMPLE 4

The complete procedure of Example 3 was repeated, except with one difference: the yeast extract was supplied at a constant rate of 14.3 mg nitrogen per kg broth per hour. This was achieved by increasing the concentration of yeast extract in the combined feed. This is 134% of the nitrogen dose of Example 3. The lovastatin acid concentration at the end of fermentation was 125% of the concentration in Example 3 (Table 1).

COMPARATIVE EXAMPLE 5 (Continuous C; batch N)

The complete procedure of Example 4 was repeated, except for the following differences: only glucose was supplied (at a rate of 1.2 g glucose per kg broth per hour). Instead of continuous feeding yeast extract together with the glucose, there was only a single yeast extract dosage to the batch medium of 36.1 g/kg. This is equivalent to the total nitrogen dosage of Example 4. The lovastatin acid concentration at the end of the fermentation was only 75% of that obtained in Example 4, and equivalent to that produced in Comparative Example 6 (table 1).

COMPARATIVE EXAMPLE 6 (batch C and N)

One 1 ml vial of a spore suspension of *Aspergillus terreus* strain AD43 as used in Example 1, stored in glycerol at −80° C. was opened aseptically, and contents were suspended in a 2 liter shake flask containing 500 ml of the following medium (500 ml medium; sterilised for 20 minutes at 121° C.)

| Ingredient | Amount per liter |
|---|---|
| Glucose | 10 g |
| Oat meal | 10 g |
| Tomato paste | 40 g |
| Corn steep liquor | 5 g |
| Trace elements | 1 ml |

The trace elements solution contains: $FeSO_4.7H_2O$, 1 g; $MnSO_4.1H_2O$, 1 g; $CuCl_2.2H_2O$, 0.025 g; $CaCl_2.2H_2O$, 0.1 g; $H_3BO_4$; 0.056 g; $(NH_4)_6Mo_7O_{24}.4\ H_2O$, 0.019 g; $ZnSO_4.7H_2O$, 0.2 g per liter.

The shake flask was incubated at 28° C. during 24 hours in a rotary shaker at 220 rpm. The complete content of 1 shake flask (500 ml) was then inoculated into a fermenter with 10 kg of medium. The composition of the fermentation broth was as follows (sterilised for 45 minutes at 121° C.)

| Ingredient | Amount per kg |
|---|---|
| Glucose | 75 g |
| Yeast extract | 11 g |
| Glycerol | 5 ml |
| $KH_2PO_4$ | 4 g |
| Soybean oil | 2 ml |
| Sodium acetate | 1 g |
| $FeSO_4.7H_2O$ | 5 mg |

Fermentation conditions were as follows:
pH was not regulated in this fermentation;
temperature was controlled at 28° C.;
the broth was agitated and aerated, keeping the dissolved oxygen level above 40% of saturation (as in all other fermentations);

The results of lovastatin production are shown in Table 1.

The feeding of glucose only (Comparative Example 5), with all the nitrogen included at the start of the fermentation, seems to have given no advantage over the batch (for both C and N) process in Comparative Example 6 as a similar yield of lovastatin was obtained. It appears therefore that it is the feeding of nitrogen that provides increased yields. This is a surprising observation, considering that lovastatin does not contain nitrogen.

EXAMPLE 7

One 1 ml vial of a spore suspension of *Penicillium citrinum* strain ATCC 38065, stored in glycerol at −80° C. was opened aseptically, and the contents suspended in a 2 liter shake flask containing 500 ml of the following medium (sterilised for 20 minutes at 120° C.:

| Ingredient | Amount per kg |
|---|---|
| glucose | 10 g |
| oatmeal | 10 g |
| tomato paste | 40 g |
| cornsteep liquor | 5 g |
| trace elements | 1 ml |

The trace elements solution contains: $FeSO_4.7H_2O$, 1 g; $MnSO_4.1H_2O$, 1 g; $CuCl_2.2H_2O$, 0.025 g; $CaCl_2.2H_2O$, 0.1 g; $H_3BO_4$, 0.056 g; $(NH_4)_6Mo_7O_{24}.4\ H_2O$, 0.019 g; $ZnSO_4.7H_2O$, 0.2 g per liter.

The shake flask was incubated at 24° C. in a rotary shaker at 220 rpm for 24 hours. The complete contents of the flask (500 ml) was then inoculated into a fermenter with 10 kg of a medium. The composition of the fermentation broth before inoculation and the glucose and ammonia feed rates were the same as described in Example 1.

The fermentation was begun with the conditions as follows:

the pH was maintained above a minimum value of 4.0;
the temperature was 24° C.;
the air supply was 0.9 volumes of air per volume broth per minute; and
the broth was agitated.

The compactin yield obtained was 110% of that in Comparative Example 9 (see Table 2).

EXAMPLE 8

A seed culture of *Penicillium citrinum* strain ATCC 38065 was prepared as described in Example 7. The contents of one flask (500 ml) was then inoculated into a fermenter with 10 kg of medium. The composition of the fermentation broth and the glucose and yeast extract feed rate were as described in Example 4. The fermentation conditions were as given in Example 7.

The compactin production was 150% of that in Comparative Example 9, as shown in Table 2.

COMPARATIVE EXAMPLE 9: (batch C and N)

A seed culture of *Penicillium citrinum* strain ATCC 38065 was prepared as described in Example 7. The contents of one flask (500 ml) was then inoculated into a fermenter with 10 kg of medium. The composition of the fermentation broth was as described in Comparative Example 6.

The fermentation conditions were as follows:
the pH was maintained above 4.0;
the temperature was controlled at 24° C.; and
the broth was agitated and aerated, keeping the dissolved oxygen level above 40% of saturation.

In this process only 29 mg/kg compactin was reached, as shown in Table 2.

TABLE 2

| Example | C/N ratio fed (g/g) | Compactin yield (mg/kg) | % relative to Comparative Example 9 |
|---|---|---|---|
| 7 | 19 | 32 | 110 |
| 8 | 34 | 44 | 150 |
| Comp. 9 | — | 29 | 100 |

As will be realised when comparing the above with the lovastatin Examples 1 and 4, a positive effect of a feed of glucose and nitrogen was also observed on compactin levels, with similar productivity increase relative to the batch culture situation.

The unexpected benefits of high production levels of lovastatin by means of a nitrogen feed have been shown here to apply generally to the production of statins.

The calculation of the carbon to nitrogen ratio fed to the culture in the various examples is presented in Table 3.

TABLE 3

| Example | Glucose (g/kg/hr) | C (mg/kg/hr) | N (mg/kg/hr) | C/N (g/g) |
|---|---|---|---|---|
| 1, 7 | 1.35 | 540 | 28.6 | 19 |
| 2 | 1.35 | 540 | 14.3 | 38 |
| 3 | 1.2 | 480 | 10.7 | 45 |
| 4, 8 | 1.2 | 480 | 14.3 | 34 |
| (comp) 5 | 1.2 | 480 | - (batch) | — |
| (comp) 6, 9 | - (batch) | — | - (batch) | — |

What is claimed is:

1. A process for the preparation of a compound of the formula

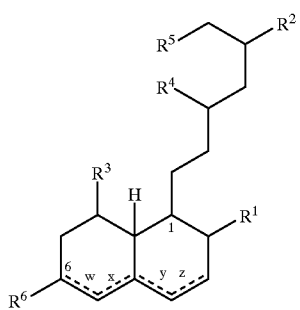

I wherein $R^1$ and $R^2$ are individually selected from the group consisting of hydrogen, —OH, alkyl of 1 to 10 carbon atoms, alkoxy of 1 to 10 carbon atoms, cycloalkyl of 3 to 10 carbon atoms and aryl of 6 to 10 carbon atoms and aralkyl of 7 to 11 carbon atoms, the latter two optionally containing at least one hetero atom, $R^3$ is $R^1CO$— or $R^1COO$—, $R^4$ and $R^5$ are individually selected from the group consisting of hydrogen, —$OR^1$, —$COR^1$ and —COOR", R" is selected from the group consisting of hydrogen, alkyl of 1 to 10 carbon atoms, cycloalkyl of 3 to 10 carbon atoms and aryl of 6 to 10 carbon atoms and aralkyl of 7 to 11 carbon atoms, the latter two optionally containing at least one hetero atoms or $R_4$ and $R_5$ together with the carbon atoms form a six membered ring having one or two oxygen atoms, $R^6$ is selected from the group consisting of hydrogen, —OH and alkyl of 1 to 10 carbon atoms, the alkyl, alkoxy, cycloalkyl, aryl and aralkyl may be substituted with at least one member of the group consisting of halogen, —$CF_3$, —OH and alkoxy of 1 to 4 carbon atoms, w, x, y and z individually represent 0, 1 or 2 double bonds with the proviso that combination w and x, x and y, y and z independently represent maximally one double bond and a salt or isomer thereof comprising culturing a microorganism in a culture medium comprising an assimilable nitrogen source and an assimilable carbon source to allow the microorganism to produce the compound of Formula I wherein at least part of the nitrogen source is continuously or intermittently supplied to the culture with the proviso that the nitrogen source is not supplied to the culture continuously at a rate of 3.5 mg of a nitrogen per kg of culture per hour.

2. The process of claim 1 wherein $R^1$ is hydrogen.

3. The process of claim 1 wherein $R^3$ is

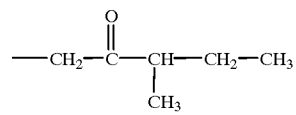

and $R^6$ is selected from the group consisting of hydrogen, —OH and —$CH_3$.

4. The process of claim 1 wherein $R^4$ is —OH and $R^5$ is —COOH or $R^4$ and $R^5$ together form

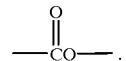

5. The process according to claim 1 wherein at least a part of the carbon source is also supplied to the culture medium continuously or intermittently.

6. The process according to claim 5 wherein the nitrogen and carbon sources are supplied independently from separate feed vessels.

7. The process according to claim 1, wherein the nitrogen source is supplied to the culture at substantially the same rate as consumed by the microorganisms present in the culture.

8. The process according to claim 5, wherein the nitrogen and carbon sources are supplied to the culture at substantially the same rate as consumed by the microorganisms present in the culture.

9. The process according to claim 1 wherein the C:N weight ratio supplied to the culture is at least 10:1 and/or less than 130:1.

10. The process according to claim 1 wherein the relative rate of supply of nitrogen to carbon is varied during the process.

11. The process according to claim 1 wherein the nitrogen source comprises yeast extract and/or ammonia, and the carbon source comprises glucose.

12. The process according to claim 1 wherein, prior to the production process, the microorganism is subjected to one or more seed phase(s).

13. The process according to claim 1 wherein the microorganism is a fungus.

14. The process according to claim 1 wherein the microorganism is of the genus Aspergillus, Monascus and/or Penicillium.

15. The process according to claim 1 wherein the microorganism is of the strain *Aspergillus terreus, Monascus anka, Monascus purpureus, Monascus ruber, Monascus vitreus, Monascus paxii* and/or *Penicillium citrinum*.

16. The process according to claim 1 wherein the conditions are such that the nitrogen concentration present in the culture is minimised.

17. The process according to claim 1 wherein the compound is an HMG-CoA inhibitor.

18. A process according to claim 1 wherein the compound is lovastatin, pravastatin or compactin.

* * * * *